(12) United States Patent
Mayer et al.

(10) Patent No.: US 12,369,937 B2
(45) Date of Patent: Jul. 29, 2025

(54) SURGICAL APPARATUS, SURGICAL SYSTEM AND METHOD OF SETTING UP A SURGICAL APPARATUS

(71) Applicant: WOODWELDING AG, Stansstad (CH)

(72) Inventors: Jörg Mayer, Niederlenz (CH); Domenico Romeo, Wohlen (CH); Dominique Neuhaus, Zürich (CH); Andrè Schwery, Biberist (CH); Lutz Beerstecher, Borex (CH); Jan Beerstecher, Fétigny (CH)

(73) Assignee: WOODWELDING AG, Stansstad (CH)

( * ) Notice: Subject to any disclaimer, the term of this patent is extended or adjusted under 35 U.S.C. 154(b) by 1094 days.

(21) Appl. No.: 17/298,761

(22) PCT Filed: Dec. 2, 2019

(86) PCT No.: PCT/EP2019/083325
§ 371 (c)(1),
(2) Date: Jun. 1, 2021

(87) PCT Pub. No.: WO2020/114974
PCT Pub. Date: Jun. 11, 2020

(65) Prior Publication Data
US 2022/0054161 A1    Feb. 24, 2022

(30) Foreign Application Priority Data
Dec. 3, 2018    (CH) .................................. 01488/18

(51) Int. Cl.
*A61B 17/32*     (2006.01)
*A61B 17/16*     (2006.01)
*A61B 17/00*     (2006.01)

(52) U.S. Cl.
CPC .. *A61B 17/320068* (2013.01); *A61B 17/1626* (2013.01); *A61B 2017/00973* (2013.01); *A61B 2017/1651* (2013.01)

(58) Field of Classification Search
CPC ...... A61B 17/16; A61B 17/1644; A61B 17/32; A61B 17/320068; A61B 2017/00973;
(Continued)

(56) References Cited

U.S. PATENT DOCUMENTS

| | | | |
|---|---|---|---|
| 2002/0038102 A1* | 3/2002 | McFarlin | A61B 17/1626 606/167 |
| 2002/0111608 A1* | 8/2002 | Baerveldt | A61F 9/00781 606/49 |

(Continued)

FOREIGN PATENT DOCUMENTS

| | | |
|---|---|---|
| JP | 2002-200094 A | 7/2002 |
| JP | 2004-508874 A | 3/2004 |

(Continued)

OTHER PUBLICATIONS

English translation of Chinese Office dated Feb. 29, 2024, Application No. 201980079100.9; 10 pages.

*Primary Examiner* — Eric S Gibson
(74) *Attorney, Agent, or Firm* — Rankin, Hill & Clark LLP

(57) ABSTRACT

A surgical apparatus generates energy that is input onto an appliance. The appliance is one of an implant to be implanted in human or animal bone tissue by the input of the energy, and of a tool being an ultrasonic bone cutting and/or punching tool for cutting and/or punching living human or animal bone tissue by input of energy onto the implant in a surgical operation. The apparatus includes a control device and at least one handpiece, the handpiece being equipped to be held by a surgeon during the operation and to couple the energy into the appliance. The apparatus further includes a (Continued)

reading device equipped to read out, from an appliance data carrier, appliance data dedicated to the appliance. The control device checks, depending on the appliance data, whether the handpiece is suitable for the appliance and chooses operating parameters depending on the appliance data.

24 Claims, 2 Drawing Sheets

(58) Field of Classification Search
CPC  A61B 2017/1651; A61B 2017/320072; A61B 2017/320073; A61B 2018/00988; A61B 90/94; A61B 2090/0803
See application file for complete search history.

(56) References Cited

U.S. PATENT DOCUMENTS

| | | | |
|---|---|---|---|
| 2003/0093103 A1* | 5/2003 | Malackowski | A61B 34/20 606/170 |
| 2005/0065542 A1 | 3/2005 | Mansfield | |
| 2005/0096679 A1* | 5/2005 | Stulen | A61B 17/320068 606/169 |
| 2011/0196286 A1* | 8/2011 | Robertson | A61B 17/320068 606/169 |
| 2013/0289592 A1* | 10/2013 | Stulen | A61B 17/320092 606/169 |
| 2014/0031726 A1* | 1/2014 | Chernomorsky | A61N 7/00 601/2 |
| 2014/0039495 A1* | 2/2014 | Bonutti | A61F 2/46 606/60 |
| 2014/0128863 A1* | 5/2014 | Du | A61N 7/00 606/34 |
| 2014/0277568 A1* | 9/2014 | Baehre | A61L 31/10 424/423 |
| 2015/0164531 A1* | 6/2015 | Faller | A61B 17/320092 606/169 |
| 2015/0272608 A1* | 10/2015 | Gladstone | A61B 17/1622 606/167 |
| 2017/0340345 A1* | 11/2017 | Yates | A61B 17/3211 |
| 2022/0054161 A1* | 2/2022 | Mayer | A61B 90/98 |

FOREIGN PATENT DOCUMENTS

| | | | |
|---|---|---|---|
| JP | 2009-153989 A | 7/2009 | |
| WO | 02/069817 | 9/2002 | |
| WO | 03/013372 | 2/2003 | |
| WO | 2008/034277 | 3/2008 | |
| WO | 2009/055952 | 5/2009 | |
| WO | 2009/132472 | 11/2009 | |
| WO | 2010/045751 | 4/2010 | |
| WO | 2011/054124 | 5/2011 | |
| WO | WO-2016123179 A1 * | 8/2016 | A61B 17/320068 |
| WO | 2017/106329 A1 | 6/2017 | |
| WO | 2020/007865 | 1/2020 | |

* cited by examiner

SURGICAL APPARATUS, SURGICAL SYSTEM AND METHOD OF SETTING UP A SURGICAL APPARATUS

BACKGROUND OF THE INVENTION

Field of the Invention

The invention is in the field of medical technology. More particularly, it relates to a surgical apparatus for implanting an implant in human or animal tissue and/or for cutting and/or punching human or animal living bone tissue.

Description of Related Art

WO 02/069 817, WO 2011/054124 and other publications teach a method of implanting an implant that is based on the following principle. The implant includes a liquefiable, for example thermoplastic, material in a solid state. Mechanical vibration energy is used to impinge on the thermoplastic material until a portion thereof is liquefied. The liquefied material is pressed into structures of hard tissue (especially bone tissue) and after re-solidification anchors the implant. For this approach, there are especially two categories of implant: implants of a first category have an implant surface or at least a portion of an implant surface including the thermoplastic material. For the anchoring process, the implant is pressed against the tissue (or in embodiments against a counter element while being close to the tissue) until the material becomes flowable. If belonging to a second category, the implant includes a body of a not liquefiable material with a hollow space, and a liquefiable element is pressed into the body while the mechanical vibration energy is applied until at least a part of the liquefiable element becomes liquid, and the liquefied thermoplastic material is pressed through at least one opening of the hollow space into surrounding tissue to anchor the implant. Both categories may optionally be combined with conventional anchoring means, such as an outer thread of the implant or similar. There are further variants, including variants in which the sonotrode is subject to a pulling force, as for example explained in WO 2008/034 277, WO 2009/055 952, WO 2009/132 472, WO 2010/045 751.

Both, the instrument for applying the mechanical vibration energy as well as the parameters to be applied during the implantation depend on the implant and the related sonotrode. There are not only differences between the two named categories but also differences depending on dimensions, materials, shapes and possibly other parameters, including indication dependent parameters. The surgeon or her/his team before operation has to choose an appropriate combination of an implant and an instrument, make sure that the instrument is ready and in good condition, program or select appropriate settings of the instrument and has to apply, during operation, the correct parameters. This necessitates some effort and may be a cause of mistakes.

It has also become known to use ultrasonic vibration for bone cutting or microfracturing. To this end, an ultrasonic cutting and/or punching tool is used. Such cutting and/or punching tool may be coupled to a vibration generating instrument. Also in this case, the instrument and the operation parameters depend on the particular cutting and/or punching tool, and the surgeon and his/her team before operation has to make the corresponding choice. Cutting and punching tools often need cooling in order to avoid necrosis and damage to the tool due to overheating. Also the cooling level needs to be chosen by the surgeon and his/her team.

WO 03/013372 discloses a surgical power tool system with a control console and a handpiece powered by the control console. An accessory, such as a cutting accessory, is coupled to the handpiece. The accessory includes an identification chip that describes the operating and/or physical characteristics of the accessory. The handpiece includes coils that enable the handpiece to read data in the accessory by inductive coupling. This set-up requires that the readout coils and associated electronics in the handpiece are relatively large (in case the identification chip in the accessory is small) and relatively close to the physical interface with the accessory. Both, relatively large handpieces and readout equipment close to the physical interface are not readily implementable for all applications. Also, the identification chip needs to be sterilizable, and the materials both, of the accessory and of the handpiece, must not be electrically conducting.

US 2014/0039495 discloses methods of securing a fastener by means of ultrasonic vibration. US 2014/0039495 mentions that the fastener may have an embedded RFID tag.

US 2014/0031726 discloses low frequency ultrasound surgical systems for the treatment of soft tissues. The systems may include an ultrasound device coupled to a generator, and a distal functional tip. The distal functional tip may have an embedded communication device, such as an RFID or NFC device. In an example, a communication unit of the ultrasound device communicates with the communication device of the distal functional tip and reports to the generator which kind of distal functional tip is currently coupled to it. Based on this information, the generator may reconfigure the electrical signals to be applied to the transducers within the ultrasound device.

All these approaches have in common that the respective hand-worn part of the system requires a readout device, and that the part that comes into close contact with body tissue (the accessory/fastener/distal functional tip), and which therefore needs to be sterilizable, has to carry a chip.

SUMMARY OF THE INVENTION

It is therefore an object of the present invention to provide an instrumentation and method overcoming drawbacks of the prior art and especially making the preparation of the system for implantation or bone cutting and/or punching more easy and/or more secure.

According to an aspect of the invention, a surgical apparatus for implanting an implant by input of energy onto the implant in a surgical operation and/or for cutting and/or punching human or animal living bone tissue by an ultrasonic tissue treatment tool is provided, the apparatus including a control device and at least one handpiece, the handpiece being equipped to be held by a surgeon during the operation and to couple the energy into the implant or tool, respectively, wherein the apparatus includes a reading device equipped to read out, from an appliance data carrier, appliance data dedicated to the implant or tool, respectively, wherein the control device is equipped and programmed to carry out a check, depending on the appliance data, whether the handpiece is suitable for the implant or tool, respectively and to choose (settable) operating parameters depending on the appliance data.

The check whether the handpiece is suitable for the implant or tool may optionally include a check of the entire chain of vibrating elements, including the sonotrode (does it fit to the handpiece and to the implant, if applicable) or, in the case of bone cutting the entire system including the used blade.

The appliance data carrier may be an implant data carrier or a tool data carrier.

An ultrasonic tissue treatment tool may especially be a bone cutting tool, i.e. a tool for bone cutting and/or bone punching. However, it may also be a drilling tool, abrading tool, debriding tool, cauterization tool, etc.

The apparatus may in embodiments especially be configured for both, for implantation and for tissue treatment (bone cutting/punching, etc.), with the energy being mechanical vibration energy. The apparatus may then be configured to choose operating parameters for implantation if the recognized appliance is an implant, and to choose operating parameters for bone cutting/punching if the recognized appliance is a bone cutting/punching tool.

However, it is also possible that the apparatus is specialized for implantation only or for example for bone cutting/bone punching only.

If the appliance is an implant and the energy is mechanical vibration energy, the handpiece is equipped or needs to be equipped with a sonotrode having an outcoupling face for coupling the vibration energy into the implant. The sonotrode may depend on the implant. In embodiments, the information on the recognized implant type is outputted, and the surgeon or someone of her/his team is requested to choose an appropriate sonotrode and/or to examine whether an already present sonotrode is in fact suitable.

According to a first possibility, the surgeon may choose the sonotrode from a list of possible sonotrodes. To this end, the apparatus may output, in addition to the information on the recognized implant, also information on suitable sonotrode types.

According to a second possibility, the sonotrode—or a package thereof—may include a data carrier, too (sonotrode data carrier), and information on the sonotrode may be read out by the reading device, too, sequentially with the appliance. In this embodiment, the apparatus will issue a warning and/or will not be ready for carrying out the operation if the read out information indicates that the sonotrode does not match the implant and/or is not suitable for the chosen handpiece.

According to a third possibility, an algorithm recognizes which sonotrode is on the handpiece, for example by comparing an oscillation characteristic (natural frequency, no-load power) of the sonotrode with an according characteristic received from the appliance data carrier.

According to an even further, fourth possibility, the appliance is specified to be implanted/used in a certain way and together with a particular sonotrode. The same appliance (implant) may then be provided in different packages, depending on the indication, which indication defines the sonotrode to be used. For example, one particular implant may be implanted in open surgery with a short sonotrode, whereas it may also be implanted with a long sonotrode, for example endoscopically. The settable operating parameters differ between these two indications, and the implant will come in different packages if to be used for open surgery or endoscopically, with the packages carrying appliance data carriers with accordingly different appliance data.

The appliance data according to a first option may include the settable operating parameters, i.e. the apparatus extracts these operating parameters from the appliance data. The settable operating parameters may in embodiments be given in dependence on a sonotrode used, wherein the information on the type of sonotrode is for example obtained in one of the above-explained ways.

Providing the operating parameters as part of the appliance data features the advantage that a given surgical apparatus according to the invention will always be capable of operating with the appropriate parameters even if operated on a new type of appliance (implant, bone cutting/punching tool) that did not exist at the time the surgical apparatus was delivered. The same advantage is present if an operation regime for a certain appliance is updated.

In addition or as an alternative, according to a second option, the appliance data may identify the type of the appliance. The settable operating parameters for different types of appliances may then be stored in a memory of the surgical apparatus (which for example is regularly updated) or is accessible for the apparatus via an external storage, for example the cloud or a dedicated server accessible via a network.

In addition or as an alternative to including the settable operating parameters and/or the type of appliance, the appliance data may include an identification of the appliance, which may for example include information on the production badge or even a unique appliance identifier. Thereby, it is an option to link the operating parameters, for example including data recorded during the process, such as the date of use, the time of ultrasound application (duration), power, potential errors), with the appliance and to link it via an interface to the internet with an electronic patient file.

The energy may be mechanical vibration energy. To this end, the handpiece may include a vibration generator. Especially, such vibration generator may be powered by a signal coming from the control device via a connecting line.

Further optional data portions contained in the appliance data may include control parameters for other functions than the ultrasound application, such as light, control of a flow-through valve and/or an advance (propulsion) mechanism.

The reading device may be equipped for a contactless readout process, for example an RFID readout process. Accordingly, the appliance data carrier may be equipped to be read out in a contactless manner. Especially, the appliance data carrier may be an RFID chip, especially a passive RFID chip. As an alternative, the readout process may be carried out via a different means. For example, the appliance data carrier may be an optically readable code, such as a QR code or a barcode, and accordingly the reading device then may include an according optical reader.

Optically readable codes, like RFID chips or other semiconductor based data carriers, may be configured according to either of the above-discussed first and/or second options. I.e. optically readable codes may contain operating parameters (especially codes with the potential of containing large amount of data, such as QR codes) or may contain just an ID for identifying the type (especially for example barcodes, small QR code tags, or other smaller optically readable codes).

The appliance data carrier may include one or more of an application name (text), an ID number of any handpiece the appliance works with, a name of the appliance (text), a UDI code, a batch number, a name of the handpiece that has to be used with it (text), if applicable an identification of a sonotrode to be used with it (if the appliance is an implant), operating parameters such as maximum and minimum on-times, a minimum interval between subsequent applications, a start delay, PID settings for amplitude and/or frequency control behavior, a mean resonance frequency, as well as possibly minimum and maximum resonance frequencies, of the handpiece with this particular appliance/sonotrode, a required amplitude for the application, an optimal phase position, a maximum power, as well as a use-by date of the appliance, resulting operating parameters (i.e. operating parameters that cannot be set but that result when the apparatus is run with the settable operating parameters; resulting operating parameters for example may include power consumption if the other parameters are set or a force vs. advance characteristic, etc.) expected for optimum operation and comparable to the effective resulting operating parameters and/or other data.

The reading device may belong to the control device. It may, for example, be integrated in a housing of the control device. Optionally, a readout position for the appliance data carrier to be held next to may be marked on such housing. As an alternative to being integrated in the housing of the control device, the reading device may be present in a dedicated reading device housing separate from the handpiece. Also in this case, the reading device will be communicatively connected to the control device.

Especially, it is advantageous if the reading device belongs to the control device (and for example is integrated in the housing), and the appliance data carrier is separate from the appliance itself. Such data carrier separate from the appliance may for example be integrated in the package or may be present as separate device, for example chipcard, that may be delivered in the package or together with the package or also, depending on the requirements, separately therefrom.

An appliance data carrier separate from the appliance firstly has the advantage that the appliance data carrier does not need to be in a sterile environment and hence does not need to be sterilizable. Secondly, the reading device can be relatively large, making the readout process robust: the exact position of the appliance data carrier relative to the reading device does not necessarily have to be precisely defined for the readout process to work. Thirdly, a simpler construction of the handpiece (that needs to be sterilizable) becomes possible and more flexible, since no consideration of RFID is necessary; also different handpieces can be controlled by a same control device. A fourth advantage compared to prior art solutions is that the appliance data carrier is in an environment that is not subject to the energy, especially mechanical vibration energy. There is thus less risk of damages of the appliance data carrier. An even further advantage is that in case operating parameters change, for example because of new insights gained, it is not necessary to exchange the entire appliance, but it is sufficient to provide a new appliance data carrier, for example on a chipcard sent to the operator.

Especially if the appliance data include (settable) operating parameters and if the appliance data carrier is a passive chip, such as a passive RFID chip—which combination is preferred for many applications because of being particularly safe and flexible as well as cost efficient—a large amount of data has to be transmitted from the appliance data carrier to the apparatus. For these embodiments, a large reading device brings about additional advantages. Large reading devices may readily be integrated in the control device.

For special applications, an alternative configuration may be an option. This option applies especially if the appliance is a long-time implant. In this option, the appliance data carrier may be integrated in the appliance. The reading device is then integrated in a sterilizable reading device unit that is separate from the control unit and from the handpiece. Also in such alternative configurations, the reading device can be relatively large, in contrast to prior art solutions where the reading device is integrated in the handpiece.

In many embodiments, the handpiece will be exchangeable. This means that one can choose between different handpieces adapted to different implants and/or surgical indications, and/or that the handpiece can replaceable for example to be replaced after a certain number of uses.

The control device may further be equipped to automatically identify the handpiece, for example via a connecting line connecting the handpiece to the control device. To this end, the handpiece may include a handpiece information carrier, such as a chip with a memory, and the control device may be capable of reading out information from the handpiece information carrier. In addition, the control device (and/or optionally the handpiece itself) may be equipped to output a message and to not operate if the handpiece is not suitable for the implant. For example, the appliance data may include data on suitable handpieces and/or on parameters of suitable handpieces, such as size, power, resonance properties, etc.

In addition or as an alternative, the apparatus may be equipped to have stored and/or read out from the handpiece wear data indicating how often the handpiece had been used before and whether a revision would be necessary. The control may optionally be programmed to issue a message and to not operate if the wear data indicate that the handpiece should not be used any more (without prior revision).

In addition or as an even further alternative, the control device may for comparing resulting operating parameters with expected values. For example, the read out appliance data may include a set of expected resulting operating parameters, and the control device may detect, by comparison of the expected resulting operating parameters, whether the process was successful. For example, by comparing an expected force and/or power vs. advance characteristic with pre-set values, the control device may estimate the amount of polymer material that has been successfully pressed into surrounding tissue. If this amount is below an expected value, a warning may be issued, and the surgeon may decide whether it is necessary to repeat the implantation or not.

The apparatus may, in addition to the handpiece, include an operating control device by which the user can activate the handpiece. To this end, the operating control device may include an input tool. Especially, such operating control device may be capable of being handled by foot. Especially, such operating control device may include a foot petal. The operating control device may be configured to be operated by the surgeon carrying the handpiece. Especially, the operating control device may be connected to the control device by a sufficiently long operating control device line and/or to be in wireless communication with the control device.

The operating control device serves for operating the power during operation, i.e. the surgeon can activate, by the operating control device, the power output by the handpiece.

As an alternative to including a foot operated operating control device, an operating control may belong to the handpiece. For example, the handpiece may include a pushbutton or lever or the like for switching the power on and off.

In both cases, and generally, the operating control may be used to activate and de-activate the handpiece. However, operating parameters, such as power, frequency, etc., optionally as a profile, may be dependent on the appliance chosen and be set according to the approach taught herein, especially by belonging to the read out appliance data or by being chosen dependent on an appliance type information extracted from the appliance data.

In embodiments, the apparatus includes a cooling device equipped for cooling the appliance or a tool (such as a sonotrode) coupled to the sonotrode. These embodiments may especially be embodiments in which the appliance is an ultrasonic bone cutting and/or punching tool. In these embodiments, the control device may be equipped to control a cooling power of the cooling device. Especially, the operating parameters set by the control device and for example stored in the appliance data carrier and read out therefrom may include operating parameters of the cooling device. The cooling parameters will include a cooling power that makes sure that the appliance must not be overheated independent of the way the surgeon operates it.

For example, the required cooling power for a certain appliance may, possibly in dependence on the input power—be determined in experiments. A required cooling power may be stored as part of the appliance data.

In embodiments, the control device is equipped for an operating power to be selected. Especially, the appliance data may include information allowing to set an applicable maximum and minimum power (which maximum and minimum power may vary from appliance to appliance), for example by explicitly containing maximum and minimum power, by containing a discrete number of selectable power levels etc.

The operating device may be equipped for the operating power to be set, for example by having "+" and "−" buttons, a slider, a turning knob etc. (all these control elements may optionally be virtual, for example on a touch screen if available). The control device may especially be programmed to allow setting of the operating power depending on the appliance data, i.e. it may be made sure that the operating parameter can only be set to a reasonable level, which will depend on the appliance. A reasonable level is a level at which the appliance is operational but at which damages to the appliance or handpiece or any undesired tissue necrosis or other tissue damage is avoided.

In embodiments that include both, a selectable operating power and cooling, the operating power/cooling power pairing may be chosen such that in any case damage is prevented.

In a first variant, the cooling power is set to an appliance data dependent constant, the cooling power being sufficient to cool the appliance also when the apparatus is operated at the maximum choosable operating power for this appliance.

In a second variant, the cooling power is set to a value that depends on the chosen operating power and is constant for this operating power.

In a third variant, the cooling power is selectable in a range that possibly depends on the set operating power. The cooling power range—for example defined by a finite number of cooling power levels—may be such that even at the lowest selectable cooling power undesired damages are excluded.

Selectable cooling power may or example be useful in situations where the surgeon need to reduce the cooling power for a better sight onto the operating side or increase the cooling power for example for flushing.

Special requirements may also arise in case one cooling device (one flow of cooling liquid) is used to cool, in a serial manner, both, firstly the ultrasonic transducers in the handpiece and then the blade on a cutting/punching process. The temperature of the blade will depend both, on the power level and the cooling rate, wherein due to heat absorption at the transducers, at high power levels the temperature of the cooling liquid, when it arrives at the blade, will be higher compared to low power levels. Therefore, the dependence of the blade temperature on the named parameters is more complicated in this serial cooling situation, the blade temperature possibly depending on the power level in a non-linear manner. In situations, this may be used for example for achieving a short-time high blade temperature, for example for cauterization at the end of a procedure.

In all embodiments that include a selectable operating power and/or selectable cooling power, the control device may make sure, dependent on the stored appliance data, that the apparatus is always operated in a safe range. In contrast to the prior art, the surgeon or his staff does not need to perform calculations of reasonable operating and cooling powers but may just operate in a safe mode, with settings being selectable only within the safe range.

For obtaining the appliance data and/or for programming of the apparatus, the safe range for operating power/cooling power pairings may, in an appliance dependent manner by determined by experiments or by calculations or by any combinations of these.

In embodiments, the apparatus is equipped for demanding a confirmation after the appliance type has been identified by the apparatus. For example, the apparatus may output the identified appliance type. Such output may be made via a display of the control device for example. If applicable, all relevant elements of the system may be output, for example sonotrode and implant, sonotrode and blade, etc. The apparatus may be configured to only operate after it has been confirmed that the appliance (or the entire system if applicable) is of the intended type. Thereby, the surgeon has the possibility to recognize any faulty choice of implant or faulty recognition. In this way, embodiments of the invention yield a protection control loop.

Such confirmation may be inputted, by an assisting person, directly into the control device. As an alternative, in embodiments a confirmation input has to be made via a device remote from the control device, especially via the operating control (if applicable the operating control device and/or the operating control of the handpiece etc.). The fact that in these embodiments such confirmation, in embodiments, is done via the operating control—and hence by the surgeon herself/himself may be advantageous in terms of regulatory demands and overall control. In contrast to systems where assisting persons can confirm, confirmation by the surgeon is considered more direct and hence more secure.

In embodiments, the control device with the handpiece coupled thereto is equipped for carrying out a self-scan with or without the appliance being already coupled to the handpiece. In this self-scan for example parameters like the resonance frequency—that depends on the handpiece-appliance pairing—or other specific properties are double-checked.

The invention also concerns a system including the surgical apparatus as well as at least one appliance provided with an appliance data carrier readable by the reading device. In this, the appliance is an implant of the above-described kind including thermoplastic material liquefiable by energy for anchoring the implant in bone tissue, or the appliance is an ultrasonic bone cutting and/or bone punching tool.

The appliance data carrier may especially be present in or on a package of the appliance or be provided as separate data carrier device, for example chipcard. It however is also not excluded that the appliance data carrier is present on the appliance itself. If the appliance is an implant, this may for example be on a portion thereof that during operation is de-coupled from an implant body that remains in the patient's body after operation. If the appliance is a bone cutting and/or bone punching tool, this may be on a proximal portion (head portion) thereof, which portion does not get into direct with the bone tissue during the cutting/punching process.

The invention further concerns an appliance package with an appliance of the hereinbefore specified kind, the appliance package including an appliance data carrier, the appliance data carrier containing appliance data including operating parameters for an apparatus of the above-described kind. Especially, the operating parameters may be operating parameters of a handpiece including a vibration generator and may include operating parameters of the vibration generator, for example including at least one of a vibration power, a vibration frequency, a voltage applied to the vibration generator (which voltage defines the amplitude). The operating parameters may include a development of at least one of these as a function of time, as a function of input energy and/or as a function of a path.

The apparatus may further be configured to store process data. The process data may include at least a portion of the appliance data and thus may allow to correlate the data on the measured parameters (resulting operating parameters) like power consumption, duration, path, etc. with the appliance data. The apparatus may be configured for process data to be read out directly, in real time, and/or to be stored and read out any time after the process. Readout of such data may be used by an external device, such as a computer, for analyzing the process and also for documentation. In addition, or as an alternative, as mentioned hereinbefore, the process data may be stored to become part of the patient file and/or be used by the surgeon for analysis of the success of the medical intervention.

The apparatus may thus be equipped to output, via an appropriate interface, information on the surgical operation, such as data measured during the operation. Such output may be linked to patient data and for example become part of the electronic patient file and/or be used by the surgeon for analysis of the success of the medical intervention. In addition or as an alternative, the data may be fed, for example in an anonymized manner, to a further data base that collects the collection of operation data in a patient independent manner. Thereby, a large number of implantation processes may be analyzed and optimized, or also to identify centers (hospitals or entities within hospitals for example) in which there are often problems, so that one can intervene.

The approach of outputting data measured during operation is based on the insight that ultrasonic devices provide the unique opportunity to allow to deviate many information on the success of the operation from the process parameters—without any need for patient data. For example, the implantation force and the output power can be deviated from the feedback of the apparatus, i.e. the electrical signal required for the apparatus to work in accordance with the settable operating parameters (for example at resonance, and with a pre-set amplitude, or with a pre-set power). This is in contrast to prior art tools like drills etc. Other obtainable data include a shift of the resonance frequency during implantation, as indication of the resistance by the tissue or change of geometrical dimensions, the implantation time duration (may be indicative of failures, if too short or too long), the used power spectrum etc.

The invention further concerns a method of setting up a surgical system for surgical operation, the method including the steps of:
providing a surgical apparatus for generating an energy input onto an appliance during a surgical operation, wherein the appliance is one of an implant to be implanted in human or animal bone tissue by the input of the energy, and of a tool being an ultrasonic bone cutting and/or punching tool for cutting and/or punching living human or animal bone tissue the apparatus including a control device and at least one handpiece, the handpiece being equipped to be held by a surgeon during the operation and to couple the energy into the implant;
providing the appliance and an appliance data carried assigned to the implant;
reading out appliance data from the appliance data carrier, the appliance data dedicated to the appliance;
using the appliance data to check whether the handpiece is appropriate for the appliance; and
configuring the apparatus for carrying out the surgical operation by setting operating parameters that depend on the appliance data.

Thereafter, the apparatus is ready for the operation in which the handpiece, for example powered from the control device, is used to couple the energy into the appliance, the operation control being used to activate or deactivate the energy source.

Setting the operating parameters may include using operating parameter settings belonging to the appliance data as the operating parameters. In addition or as an alternative, setting the operating parameters may include using the appliance data to identify the appliance type and using operating parameter settings stored in a memory and assigned to the appliance type as the operating parameters.

The method may comprise, after the step of reading out, the further steps of:
outputting information on a recognized appliance type of the appliance; and
checking whether a confirmation was inputted in response to outputting.

Especially, if the apparatus has an operating control, in the step of checking it is checked whether a confirmation was inputted via the operating control, for example by a double actuation.

In addition or as an alternative method may include the further step of reading out wear data from the handpiece or from an other memory storing wear data of the handpiece. To this end, the handpiece may include a handpiece data carrier. The handpiece data carrier may for example include an EPROM. In this handpiece data carrier, any use of the handpiece is recorded. The handpiece data carrier may also record revisions, and/or may be equipped to be reset in a revision. The control device may be configure to issue a warning and/or even to not activate the handpiece if the wear data indicate that a maximum number of working cycles has been exceeded.

Further data stored on the handpiece data carrier may include a handpiece ID number, a resonance frequency of the contained transducer in an original state, a calibration factor of the handpiece for balancing out different effective transducers, a production date of the handpiece, and/or the mentioned maximum number of working cycles until the handpiece has to be revised.

It is also an option to store, as part of the appliance data and/or of the handpiece data information that allows to predict an expected end-of life before the end of life has actually been reached. In this way, planning by an institution such as a hospital etc. becomes easier, in that an exchange can be organized timely. Information that may make an advance end of life warning possible may include tolerable deviations and the variation of deviations as a function of time (trend analysis) for a particular handpiece.

The method may further include the optional step of carrying out a self-scan of the handpiece, as mentioned hereinbefore.

BRIEF DESCRIPTION OF THE DRAWINGS

Hereinafter, embodiments of the invention are described referring to drawings. The drawings are schematical. They show.

DESCRIPTION OF THE PREFERRED EMBODIMENTS

Figure 1:
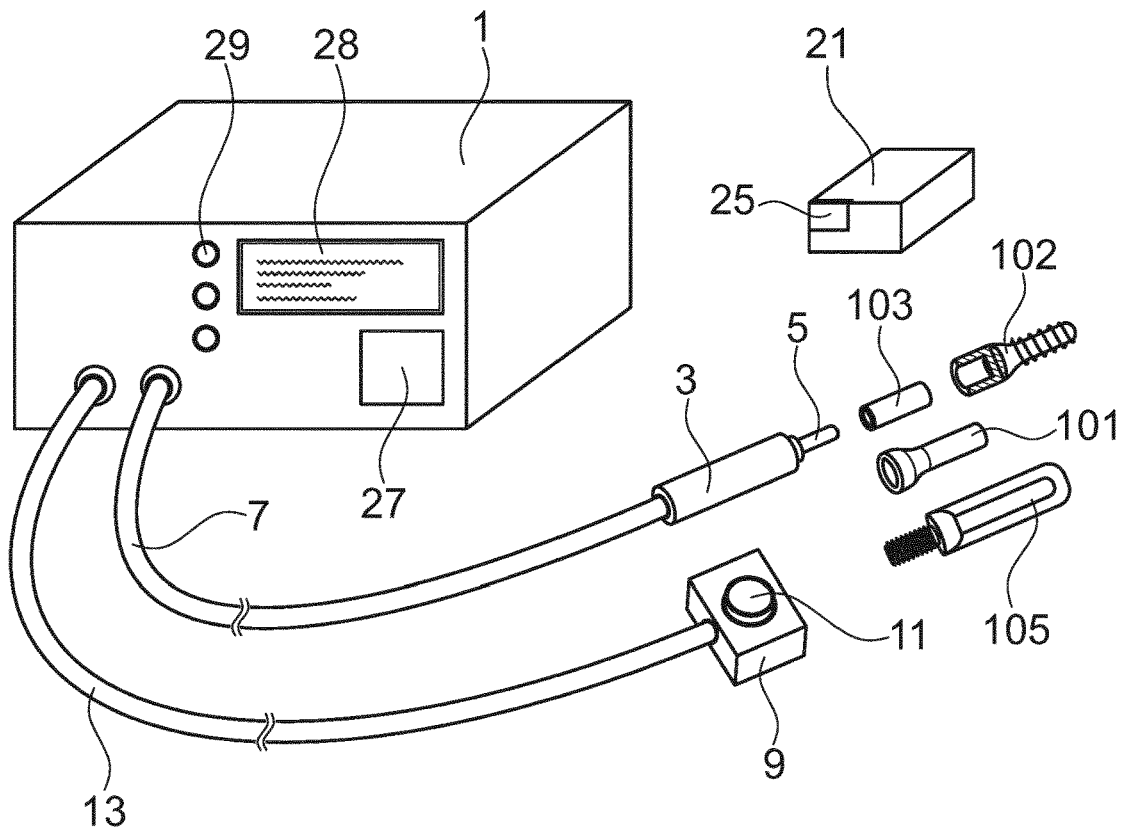
FIG. 1 an apparatus with a control device including a reader, and with a handpiece.

The apparatus shown in FIG. 1 includes a control device 1 that is connectable to a handpiece 3. The handpiece 3 for example includes a vibration generator equipped to set a sonotrode 5, 105 into mechanical installation. The electrical signal for activating the vibration generator may be supplied by the control device 1 via a connecting line 7. It may however also be possible that the control device merely transmits a command to the handpiece, and that the handpiece itself includes a control for generating the electrical signal. As yet another alternative, it would theoretically be possible that the control device 1 includes a vibration generator, and that the connecting line 7 transmits the mechanical vibration to the handpiece 3.

The apparatus further includes an operating control device 9 for the operator (i.e., generally for the surgeon). The operating control device 9 in the depicted embodiment is illustrated to be implemented as a foot operating control, especially by including a foot pedal 11. In alternative embodiments, the operating control device 9 may be present as an operating element (switch, lever or the like) of the handpiece 3. Also embodiments with a distributed operating control device including both, at least one operating element to be manipulated by foot and at least one element operated by hand are possible. Even further embodiments may include a different form of a separate operating control device.

In many embodiments, such as the depicted embodiment with a foot operating control, however, it is preferred if the person operating the handpiece also is capable of operating the operating control device. This may for example imply that the operating control device 9 is equipped to be placed in a sterile section of the operating room, i.e. remote from the—generally not sterile—control device 1. Thus, the connecting line 7 and an operating control device connecting line 13 may have a length sufficient for this; for example both, the connecting line 7 and the control device connecting line 13 may have a length of at least 2 m each. Wireless connections replacing one or both of the connecting lines are not excluded.

FIG. 1 also depicts the two categories of implants for being implanted by the device. A first category is a for example pin-shaped implant 101 including thermoplastic material at least on a portion of its surface. For example, the pin-shaped implant may consist of the thermoplastic material. For implantation, the sonotrode 5 is pressed against a proximally facing incoupling surface of the implant 101 while the implant is in contact with bone tissue and while the sonotrode 5 is subject to mechanical vibration to couple mechanical vibration energy into the implant. Due to friction between the implant and the bone tissue, the vibration energy is at least partially absorbed at the interface between the implant and the bone tissue, whereby the thermoplastic material is heated up, becomes flowable and is pressed into the bone tissue. After re-solidification, this anchors the implant in the bone tissue. See for example WO 02/069 817. A second category of implant includes a sheath element 102 with a hollow space and at least one opening through which thermoplastic material of a thermoplastic element 103 is pressable into surrounding tissue, as for example described in WO 2011/054124.

Further, FIG. 1 also depicts an alternative sonotrode 105 to be mounted to the handpiece 3, which alternative sonotrode 105 is an ultrasonic bone cutting and/or bone punching tool, for example a blade-like tool as described in the Swiss patent application 01166/18. For example, the apparatus may be equipped to support handpieces 3 for both, a sonotrode 5 for implanting an implant and for an ultrasonic bone cutting and/or punching tool. Depending on the dimensions and material parameters, it is not excluded that even a same handpiece 3 may be useable for implantation on the one hand and bone cutting/punching on the other hand.

FIG. 1 further depicts a package 21 for the appliance (implant of the first or second category or tool, depending on the planned operation) to be used, the appliance package 21 having an appliance data carrier 25 attached thereto, for example an RFID chip.

As an alternative to being present in the package, the appliance data carrier may be delivered as a separate chip card or similar, i.e. a dedicated data carrier device.

Figure 2:
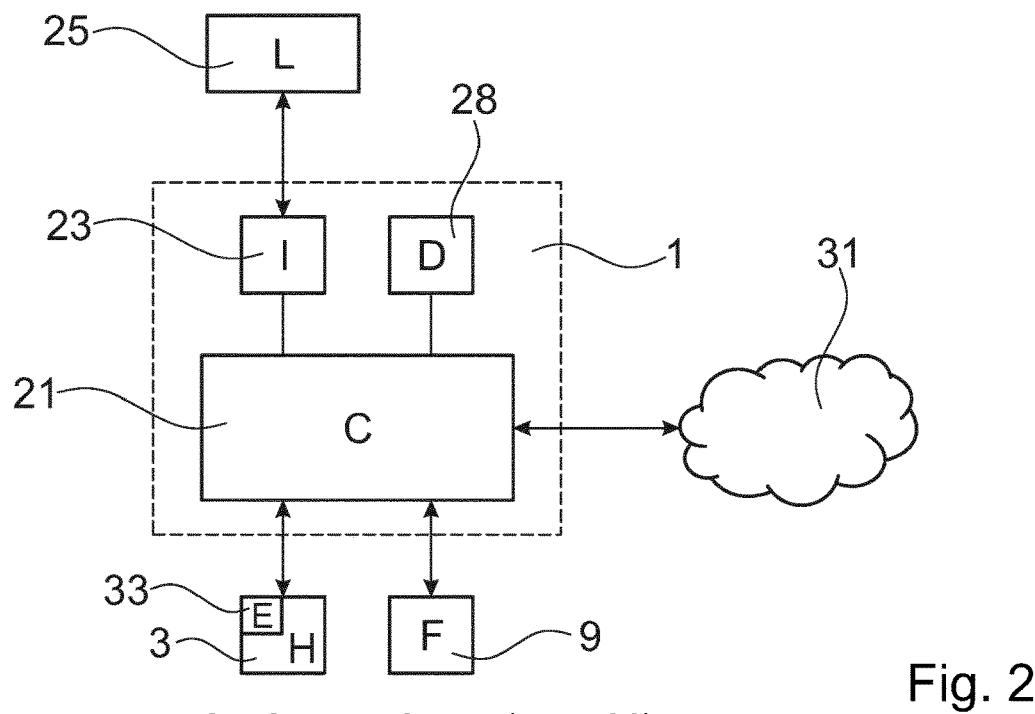
FIG. 2 a scheme of elements of the apparatus.

FIG. 2 shows a scheme of elements of the apparatus. The control device 1 includes an electronic control module 21 that is equipped to communicate with the handpiece 3 and as well as with the operating control device 9 (footpiece in the depicted embodiment). Further, it includes a communication interface module 23 that is capable of reading data from an external data carrier, namely for example an appliance data carrier 25.

The interface module may include a reader, such as an RFID reader 27, as schematically illustrated in FIG. 1. The reader is equipped to read out data from the appliance data carrier 25. The control device 1 may further include a display 28 and/or other user interface elements. In the embodiment of FIG. 1, the control device moreover has buttons 29 as part of the user interface. More in general, the user interface may include any suitable input and/or output means, including touch screen, etc.

The control device may further include a computer interface for communicating with an external computer and/or a web interface or the like for communicating directly with a computer network.

The appliance data carrier 25 may be attached to an appliance package or alternatively directly to an appliance. It contains appliance data containing information including at least one of:

identification information unambiguously identifying the appliance type;

control information containing control parameters enabling the control to control the operating process in a manner specifically adapted to the appliance type.

The appliance data carrier may have any suitable physical form, such as the form of an electronically readable data carrier, such as an integrated circuit data carrier (for example an RFID chip, i.e. an RFID transponder or RFID tag) or the form of an optically readable label (such as a QR code, barcode or other code).

If the appliance data carrier contains information allowing the identification (ID information), optionally the control may have stored control parameters of the above-disclosed kind for different implant types. The control then may select, based on the ID information, the control parameter. The control may also be equipped for using the computer interface or web interface (or the like) for obtaining the required information from the external computer or, directly or indirectly, via a network 31, for example from a dedicated server or from a cloud. The computer interface or web interface (or the like) may also serve for outputting data on the operation, for the patient's file, for analysis by the surgeon, and/or for analysis by the manufacturer and/or operator of the apparatuses for analysis.

The handpiece 3 may include a handpiece data carrier 33 that records uses of the handpiece. Such recording may include a simple counting of operations (that may be characterized by a certain working cycle being applied) or may be more complex, for example by recording a usage time, an overall (integrated) energy or even details on each individual application. Thereby, it is possible for the control device 1 to read out wear data and to make further operation dependent thereon. In addition or as an alternative, the handpiece data carrier 33 may for example include calibration data of the handpiece to warrant a correct control of the sonotrode amplitude and/or the instrument performance.

Figure 3:
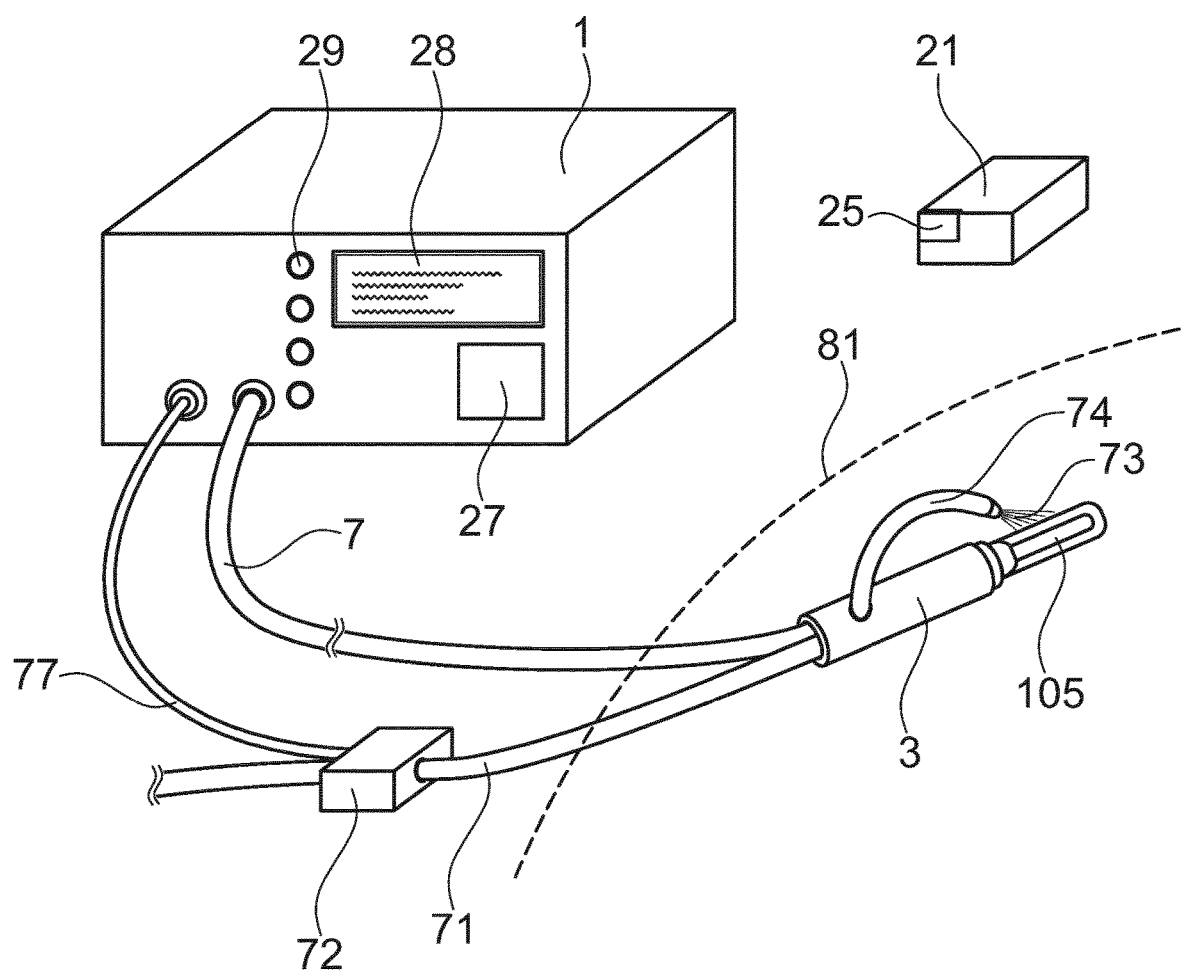
FIG. 3 an alternative apparatus.

FIG. 3 illustrates the principle that operating parameters controlled by the control device may include a cooling power. More in concrete, FIG. 3 illustrates the control device 1 connected to the handpiece 3 that carries an ultrasonic cutting tool 105 as the appliance. The handpiece is further connected to a coolant pipe 71 through which a sterile coolant (for example sterile water) is conveyed and from which the coolant 73 is sprayed (sprayhead 74) onto the cutting tool 105. A controllable pump 72 is also controlled by the control device. A controllable pump may for example be a roller pump. A separate controlling device (in addition to a controllable pump or as an alternative thereto) is possible also. The controllable pump (or other flowthrough controller) may be integrated in the control device, or be separate therefrom, as illustrated in FIG. 3

The coolant may be used for the handpiece, or the blade or both, in a serial or parallel manner. As an alternative to being sprayed onto the blade by a sprayhead, as shown in FIG. 3, it is also possible to direct the coolant through the handpiece and a cannulated sonotrode onto the blade. This latter possibility may especially be preferred if in addition to the blade also the handpiece is to be cooled.

The coolant flow controlled by the control device is dependent on the data read out from the appliance data carrier and which may, as explained hereinbefore, for example be set within limits via an input into the control device. In addition or as an alternative, (and independent of the existence of a coolant pipe) the ultrasound power may be settable within limits that depend on the data read out from the appliance data carrier, as also explained hereinbefore.

FIG. 3 also illustrates, schematically a division 81 between a sterile region in which all devices—or at least the outer surfaces of all devices—need to be sterile and a non-sterile region with the control device. If the appliance data carrier 25 is present on the package 21, the reader 27 may be in the non-sterile region.

The following process may apply for preparing the apparatus for the operation if the operation is an implantation process.

In a first step, the control device 1 checks whether the operating control device 9 (if applicable) and the handpiece 3 are present, i.e. if there is a communication link to the operating control device and the handpiece, respectively. If operating control device and/or the handpiece are equipped to be connected to the control device by a physical connecting line 7; 13, then the check includes a check whether the respective connecting lines are plugged in and whether the operating control device/the handpiece are working. If at least one of the checks has a negative result (i.e. if not both, the operating control device and the handpiece are connected and in good order), the process stops and an according message is outputted via the display and/or by other means.

In embodiments without a separate operating control device, the first step may include a check of the handpiece 3 only.

In a second, optional step, the control device reads wear data from the handpiece and for example checks whether a stored number of working cycles implies that a revision or exchange of the handpiece is necessary. If yes, an according message is output. If not, the apparatus indicates that it is ready for the process to move on to the next step.

In a third step, the appliance data (implant data) is read out. For example, to this end a person (who may be the surgeon or who may alternatively be an assisting person) holds the package (or chip card etc.) of the implant sufficiently close to the reader of the interface module. The read out step may include that the package/chip card is hold close to the reader for a certain amount of time (such as a few seconds, for example 2-5 seconds) and that after a successful readout a confirmation signal, for example an acoustic signal, is outputted.

In a fourth step, based on this appliance data the control checks whether the chosen connected handpiece is suitable for the particular implant type. If not, the apparatus outputs an according message, and the process is stopped. The information about which kind of handpiece fits to the particular implant type may be stored in the control device, may be accessible by the control device from an external source, and/or may be part of the implant data.

In a fifth, optional step, the apparatus carries out a self-scan of the handpiece, with or without the implant being already coupled thereto. In this self-scan for example parameters like the resonance frequency—that depends on the handpiece-implant pairing—or other specific properties are double-checked.

Then (if applicable if the fifth step did not yield any irregularity) in a sixth step the operator is requested to confirm that she/he is ready, for example by an appropriate input into the operating control device (such as a double click onto the foot pedal or similar). Prior to the confirmation request, the control device may output information on the implant based on the read out data, such as the type of implant, which output information is requested to be considered by the operator before confirmation. Especially, the operator or an assisting person may be requested to read the implant type from the display and to confirm only after having knowledge of the recognized implant type.

After confirmation the apparatus is ready for implantation.

After or during implantation, data may be output from the control device.

Variants of this process are possible, depending on the specific requirements and the system used.

Implantation thereafter may be possible in known manner, for example as described in WO 02/069 817, WO 2011/054124 or any other publication referring to the implantation, with the aid of mechanical vibration, of an implant including thermoplastic material.

If the appliance is an ultrasonic bone cutting and/or bone punching tool, the same process may be used, wherein instead of an implant, of a certain type, in an implant package with an implant data carrier carrying implant data, a cutting/punching tool, of a certain type, in a tool package with a tool data carrier carrying tool data is used. In the fifth, optional step then the self-scan is for example carried out with the tool coupled to the handpiece.

Operation after the preparing process may be carried out for example as known from the prior art by pressing the tool against bone tissue while mechanical vibration is coupled into the tool, to locally disrupt bone tissue for cutting/punching. In embodiments, this process may be used as microfracturing process, i.e. the bone cutting and/or punching tool may be equipped to disrupt the bone tissue only superficially in order to assist a healing process, for example as described in PCT/EP2019/067749.

What is claimed is:

1. A surgical system, comprising an apparatus, the apparatus being for generating an energy input onto an appliance during a surgical operation, wherein the appliance is one of an implant to be implanted in human or animal bone tissue by the input of the energy, and of a tool being an ultrasonic bone cutting and/or punching tool for cutting and/or punching living human or animal bone tissue, the apparatus comprising an apparatus control and at least one handpiece, the handpiece being equipped to be held by a surgeon during the surgical operation and to couple the energy into the appliance, wherein the apparatus further comprises a reader equipped to read out, from an appliance data carrier, appliance data dedicated to the appliance, wherein the apparatus control is equipped and programmed to check, depending on the appliance data, whether the apparatus is suitable for the appliance, and to choose, depending on the appliance data, operating parameters for the surgical operation, and the surgical system further comprising an appliance package releasably containing the appliance, the system further comprising the appliance data carrier readable by the reader, the appliance data carrier being integrated in the appliance package or being provided as a separate item from the appliance, whereby the appliance data carrier remains separate from the appliance when the appliance is released from the appliance package.

2. The surgical system according to claim 1, wherein the appliance data carrier is provided as a separate item contained in the appliance package.

3. The surgical system according to claim 1, wherein the appliance comprises thermoplastic material liquefiable by the energy coupled into the appliance by the handpiece.

4. The surgical system according to claim 1, wherein the reader is separate from the handpiece.

5. The surgical system according to claim 4, wherein the reader is integrated in the apparatus control.

6. The surgical system according to claim 1, the apparatus being equipped and programmed to extract at least a portion of the operating parameters from the appliance data.

7. The surgical system according to claim 1, the apparatus being equipped to extract at least a portion of the operating parameters from a data base using an appliance type information extracted from the appliance data.

8. The surgical system according to claim 1, wherein the energy is mechanical vibration energy, and wherein the handpiece comprises a vibration generator.

9. The surgical system according to claim 1, wherein the reader is equipped for a contactless readout process.

10. The surgical system according to claim 1, wherein the reader is integrated in the apparatus control.

11. The surgical system according to claim 1, wherein the reader is integrated in a sterilizable reader unit separate both, from the apparatus control and from the handpiece.

12. The surgical system according to claim 1, wherein the handpiece is exchangeable, and wherein the apparatus control is equipped to automatically identify the handpiece.

13. The surgical system according to claim 12, wherein the apparatus is equipped to output a message and/or to discontinue operation in case the handpiece is identified to be unsuitable for the appliance.

14. The surgical system according to claim 1, wherein the apparatus is equipped to have stored in a memory of the apparatus control and/or of the handpiece wear data indicating how often the handpiece had been used before and whether a revision would be necessary.

15. The surgical system according to claim 1, wherein the apparatus further comprises an operating control device separate from the handpiece and comprises an input tool, the apparatus being equipped to activate the handpiece depending on an input on the input tool.

16. The surgical system according to claim 15, wherein the input tool is a foot pedal.

17. The surgical system according to claim 1, wherein the apparatus is equipped and programmed to demand a confirmation to be inputted after an implant type of the implant has been extracted from the appliance data.

18. The surgical system according to claim 1, wherein an operating power level is adjustable by an operator, values to which the operating power level may be set depending on the appliance data.

19. The surgical system according to claim 18, wherein the apparatus further comprises a cooler equipped for cooling the appliance.

20. The surgical system according to claim 19, wherein a cooling power is adjustable by an operator, values to which the operating power level may be set depending on the appliance data.

21. The surgical system according to claim 20, wherein the values to which the operating power level may be set depending on the appliance data further depend on a power level adjusted by the operator.

22. The surgical system according to claim 19, wherein a cooling power is controlled to depend on an operating power level.

23. The surgical system according to claim 1, wherein the apparatus further comprises an interface to an external computer and/or network, wherein the apparatus is configured to output data measured during operation.

24. The surgical system according to claim 23, wherein the energy is mechanical vibration energy and the handpiece comprises a vibration generator with an ultrasonic transducer, and wherein the output data measured during operation comprises a feedback of a control of the ultrasonic transducer.

* * * * *